United States Patent
Sung et al.

(10) Patent No.: US 12,275,969 B2
(45) Date of Patent: Apr. 15, 2025

(54) **HALOPHILIC *BACILLUS AMYLOLIQUEFACIENS* KMUS1 WHICH PRODUCES THROMBOLYTIC ENZYME NATTOKINASE**

(71) Applicant: KOOKMINBIO, CORP., Jeollabuk-do (KR)

(72) Inventors: Moon Hee Sung, Seoul (KR); Misun Kwak, Goyang-si (KR); Jong-Hoon Kim, Goyang-si (KR)

(73) Assignee: KOOKMINBIO, CORP., Jeollabuk-do (KR)

( * ) Notice: Subject to any disclaimer, the term of this patent is extended or adjusted under 35 U.S.C. 154(b) by 925 days.

(21) Appl. No.: 17/288,907

(22) PCT Filed: Nov. 1, 2019

(86) PCT No.: PCT/KR2019/014706
§ 371 (c)(1),
(2) Date: Oct. 18, 2021

(87) PCT Pub. No.: WO2020/091504
PCT Pub. Date: May 7, 2020

(65) Prior Publication Data
US 2022/0033797 A1    Feb. 3, 2022

(30) Foreign Application Priority Data

Nov. 2, 2018 (KR) .......... 10-2018-0133546
Oct. 31, 2019 (KR) .......... 10-2019-0137867

(51) Int. Cl.
| | |
|---|---|
| A23L 29/00 | (2016.01) |
| A23L 11/50 | (2021.01) |
| A23L 33/135 | (2016.01) |
| C12N 1/20 | (2006.01) |
| C12N 9/54 | (2006.01) |

(52) U.S. Cl.
CPC ............... *C12N 9/54* (2013.01); *A23L 11/50* (2021.01); *A23L 29/06* (2016.08); *A23L 33/135* (2016.08);
(Continued)

(58) Field of Classification Search
USPC .......................................... 426/61
See application file for complete search history.

(56) References Cited

U.S. PATENT DOCUMENTS

2010/0021576 A1* 1/2010 Chang .................. C12N 1/205
                                                   435/252.5
2019/0098923 A1  4/2019 Park et al.

FOREIGN PATENT DOCUMENTS

CN      104877936      *  9/2015
KR   10-2013-0095127 A    8/2013
(Continued)

OTHER PUBLICATIONS

International Search Report for PCT/KR2019/014706 mailed Feb. 7, 2020 from Korean Intellectual Property Office.
(Continued)

*Primary Examiner* — Lien T Tran
(74) *Attorney, Agent, or Firm* — Revolution IP, PLLC

(57) ABSTRACT

The present invention relates to a novel halophilic *Bacillus amyloliquefaciens* KMUS1 strain (KCTC13635BP) producing thrombolytic enzyme nattokinase, and the halophilic *Bacillus amyloliquefaciens* KMUS1 strain according to the present invention produces highly active nattokinase. When food is fermented using the above strain, it can also be used in foods with high salt concentration. In addition, it can be used in the food industry through the role of dissolving and preventing blood clots by nattokinase produced by the strain.

3 Claims, 4 Drawing Sheets

(52) U.S. Cl.
CPC ...... *C12N 1/205* (2021.05); *C12Y 304/21062* (2013.01); *A23V 2002/00* (2013.01)

(56) References Cited

FOREIGN PATENT DOCUMENTS

| KR | 10-2015-0089321 A | 8/2015 |
|---|---|---|
| KR | 10-2017-0048229 A | 5/2017 |

OTHER PUBLICATIONS

Gad, R. G. et al., "Fibrinolytic Enzyme From Bacillus Amyloliquefaciens: Optimisation and Scale up Studies", International Journal of Pharmacy and Pharmaceutical Sciences, 2014, vol. 6, No. 10, pp. 370-378.

Peng, Y. et al., "Purification and characterization of a fibrinolytic enzyme produced by Bacillus amyloliquefaciens DC-4 screened from douchi, a traditional Chinese soybean food", Comparative Biochemistry and Physiology Part B: Biochemistry and Molecular Biology. 2003, vol. 134, pp. 45-52.

Choi, N.-S. et al., "The Effect of Sodium Chloride on the Serine-type Fibrinolytic Enzymes and the Thermostability of Extracellular Protease from Bacillus amyloliquefaciens DJ-4", Journal of Biochemistry and Molecular Biology, Mar. 2001, vol. 34, No. 2, pp. 134-138.

Kim, J.-H. et al., "A Novel Halostable Nattokinase of a Bacillus amyloliquefaciens KMUS1 Isolated from the Korean Jeotgal Kimchi", In: KMB 2019 46th Annual Meeting & International Symposium, poster G-8, Jun. 23-25, 2019, International Convention Center Jeju.

\* cited by examiner

[FIG. 1]
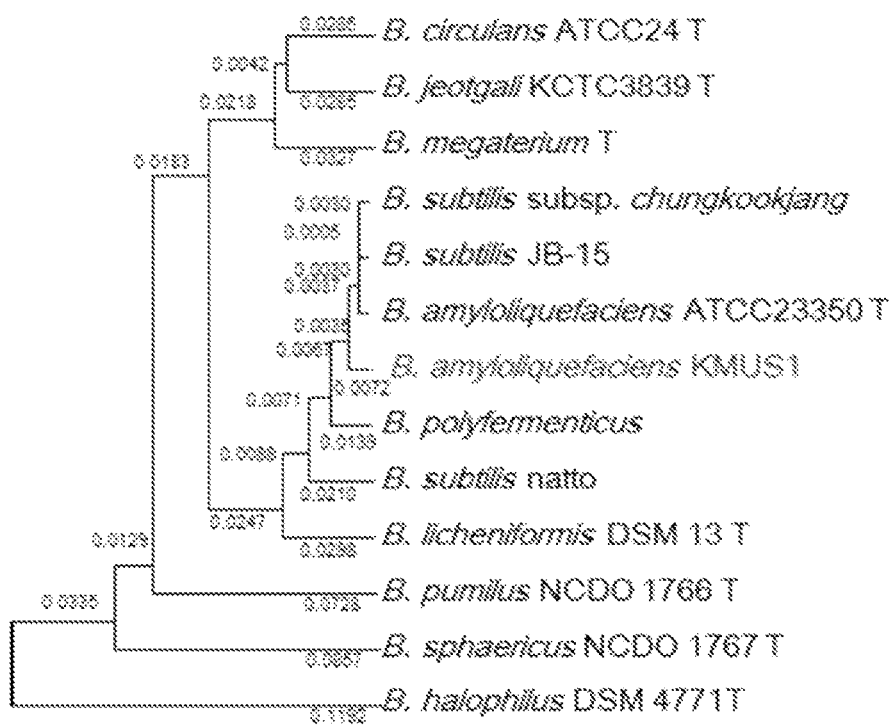

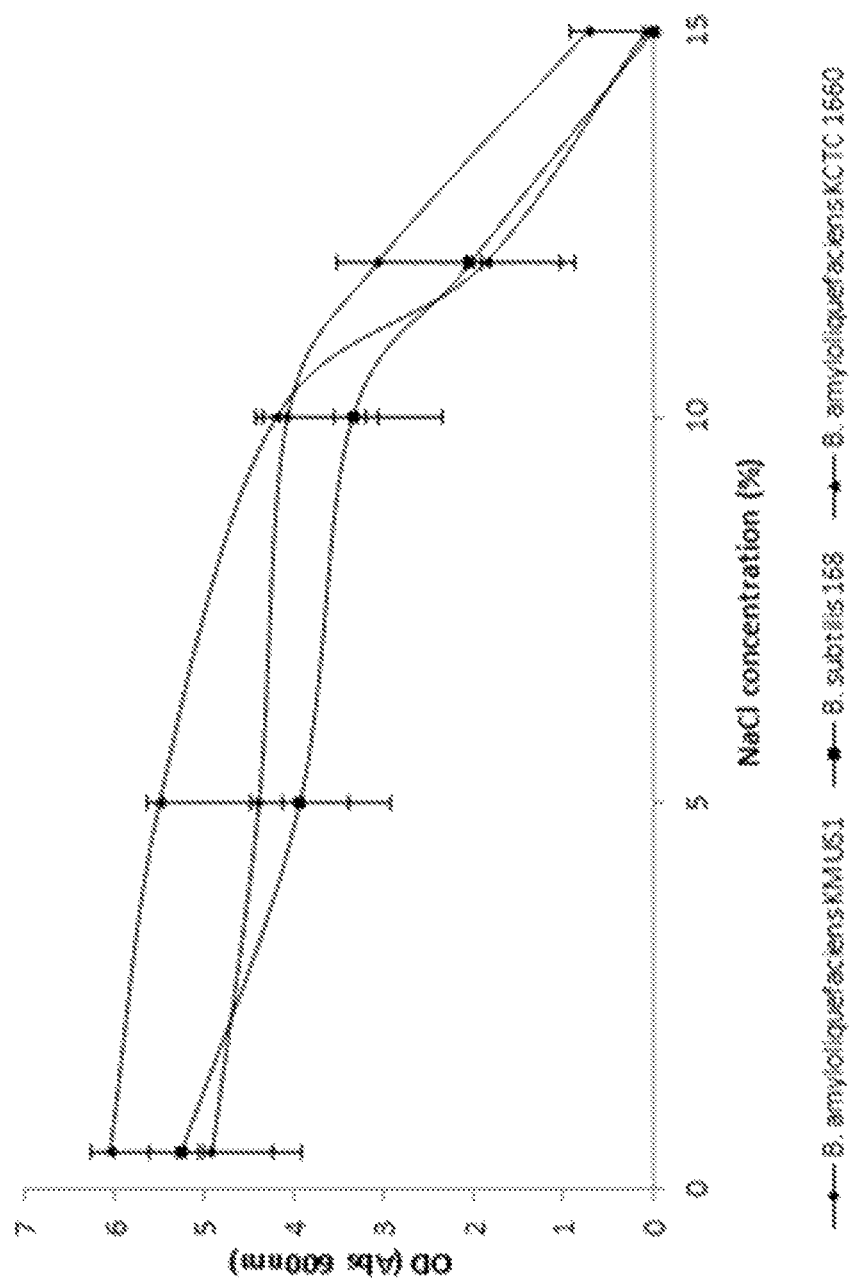
[FIG. 2]

[FIG. 3A]
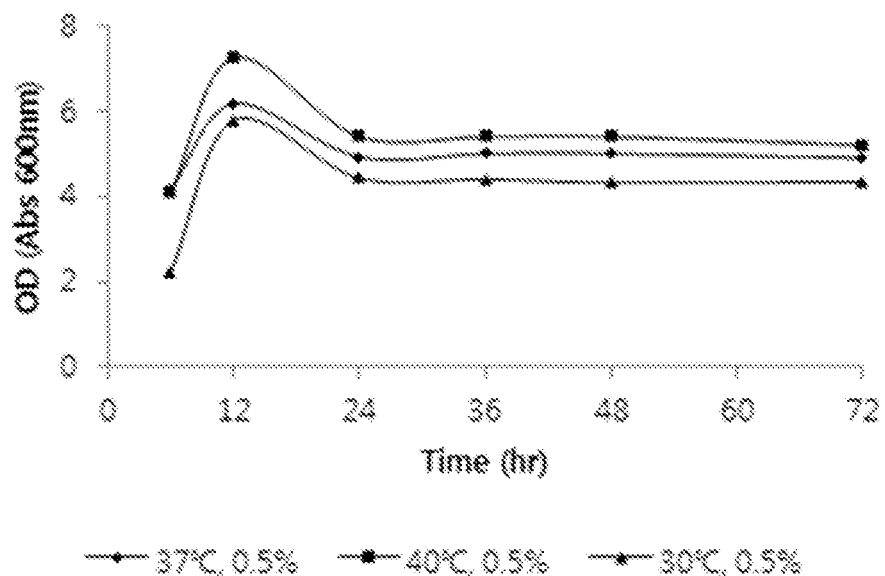
[FIG. 3B]
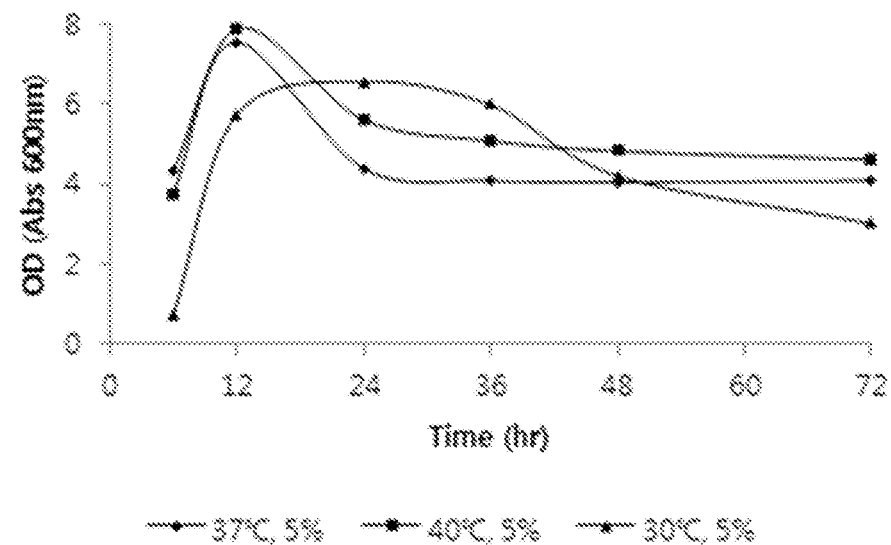

[FIG. 4]
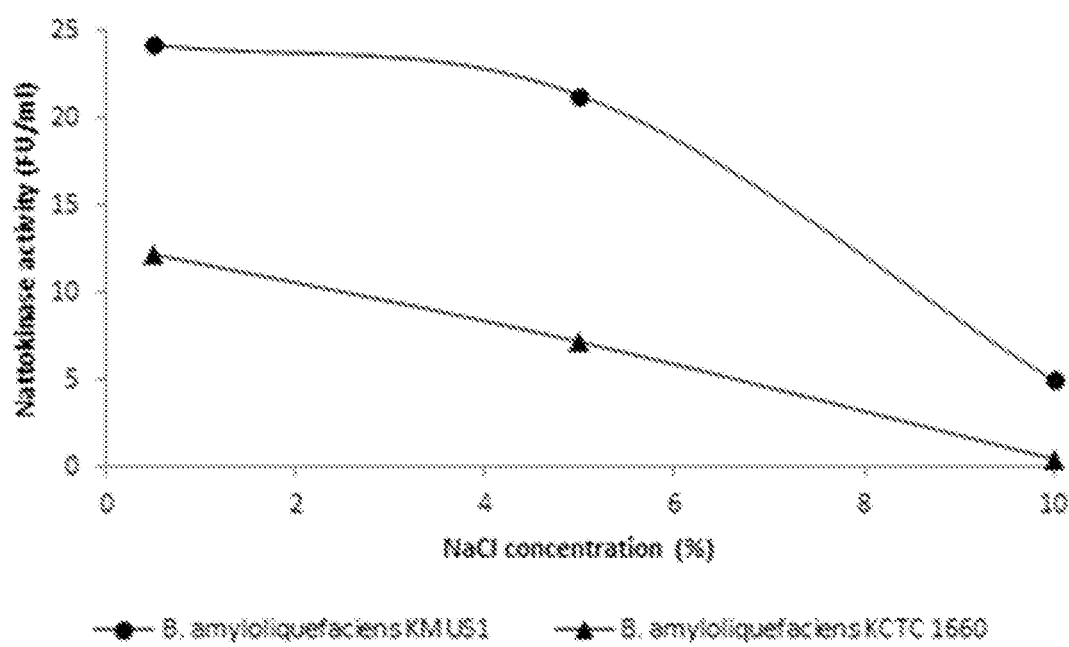

HALOPHILIC *BACILLUS AMYLOLIQUEFACIENS* KMUS1 WHICH PRODUCES THROMBOLYTIC ENZYME NATTOKINASE

CROSS REFERENCE TO PRIOR APPLICATIONS

This application is the 35 U.S.C. 371 national stage of International application PCT/KR2019/014706 filed on Nov. 1, 2019; which claims priority to Korean application 10-2018-0133546 filed on Nov. 2, 2018, and Korean application 10-2019-0137867 filed on Oct. 31, 2019. The entire contents of each of the above-identified applications are hereby incorporated by reference.

TECHNICAL FIELD

The present invention relates to a novel halophilic *Bacillus amyloliquefaciens* KMUS1 strain (KCTC13635BP) that produces thrombolytic enzyme nattokinase.

BACKGROUND ART

Nattokinase is an enzyme extracted and purified from the traditional Japanese food called "natto". Natto is a food produced by fermenting boiled soybeans by *Bacillus subtilis* natto, but during this fermentation process, various nutrients including nattokinase are produced. Since then, the enzyme that decomposes fibrin (a protein that is a source of blood clots) has been named "Nattokinase".

Nattokinase acts directly on fibrin, the main component of blood clots, to decompose (dissolve), activates prourokinase, a precursor to urokinase, a thrombolytic enzyme in the body, and increases the amount of tissue plasminogen active substance (t-PA) that produces thrombolytic enzyme plasmin. In addition, in a recent study, it was found that nattokinase has an action of decomposing the thrombolytic inhibitor PAI-1, which makes it difficult for blood clots to dissolve, and has an action of shortening the dissolution time of euglobulin, thereby enhancing thrombolytic activity. In other words, nattokinase plays an important role in dissolving existing blood clots and preventing the formation of new blood clots.

As an enzyme-producing strain that produces nattokinase, a halophilic strain is also highly likely to be utilized. *Bacillus* strains play an important role in the initial fermentation of kimchi, a fermented food. This is because enzymes produced by *Bacillus* strains break down proteins in kimchi and salted fish to produce useful peptides and enhance the flavor of kimchi. Because kimchi is fermented using salt and salted fish, the salt concentration is higher than that of general foods. Therefore, the halophilic *Bacillus* strain has a wide range of action in a fermentation environment with a high salt concentration. There are not many examples of halophilic *Bacillus* bacteria developed as highly active enzymes so far. Therefore, the halophilic *Bacillus* strain that produces a halophilic enzyme is considered to have high utility value in the food field.

DISCLOSURE

Technical Problem

An object of the present invention is to provide a novel halophilic *Bacillus amyloliquefaciens* KM US1 strain (KCTC13635BP) that produces thrombolytic enzyme nattokinase, a method of preparing thrombolytic enzyme nattokinase using the same, and a food composition, a functional food composition or a health functional food composition comprising cells, cultures obtained by culturing the strain, or an enzyme isolated and purified therefrom, as an active ingredient.

Technical Solution

In order to achieve the above object, the present invention provides a halophilic *Bacillus amyloliquefaciens* KMUS1 strain which is deposited as KCTC13635BP and produces thrombolytic enzyme nattokinase.

Also, the present invention provides a method of producing thrombolytic enzyme nattokinase culturing the halophilic *Bacillus amyloliquefaciens* KMUS1 strain.

In addition, the present invention provides a food composition comprising a bacterial body, a culture obtained by culturing the halophilic *Bacillus amyloliquefaciens* KMUS1 strain, or an enzyme isolated and purified therefrom, as an active ingredient.

Furthermore, the present invention provides a functional food composition comprising a bacterial body, a culture obtained by culturing the halophilic *Bacillus amyloliquefaciens* KMUS1 strain, or an enzyme isolated and purified therefrom, as an active ingredient.

In addition, the present invention provides a health functional food composition comprising a bacterial body, a culture obtained by culturing the halophilic *Bacillus amyloliquefaciens* KMUS1 strain, or an enzyme isolated and purified therefrom, as an active ingredient.

Advantageous Effects

The present invention relates to a novel halophilic *Bacillus amyloliquefaciens* KMUS1 strain (KCTC13635BP) producing thrombolytic enzyme nattokinase, and the halophilic *Bacillus amyloliquefaciens* KMUS1 strain according to the present invention produces highly active nattokinase. When food is fermented using the above strain, it can also be used in foods with high salt concentration. In addition, it can be used in the food industry through the role of dissolving and preventing blood clots by nattokinase produced by the strain.

DESCRIPTION OF DRAWINGS

FIG. 1 shows the phylogenetic tree of the strain of the present invention.

FIG. 2 shows a graph of comparing the sodium chloride resistance of '*Bacillus amyloliquefaciens* KMUS1', '*Bacillus amyloliquefaciens* KCTC 1660' and '*Bacillus subtilis* 168'.

FIG. 3A shows a result of growth of bacteria by temperature in 0.5% sodium chloride medium, and FIG. 3B shows a result of growth of bacteria by temperature in 5% sodium chloride medium.

FIG. 4 shows a graph of comparing the nattokinase activity according to the sodium chloride concentration of '*Bacillus amyloliquefaciens* KMUS1' and '*Bacillus amyloliquefaciens* KCTC 1660' strains.

BEST MODE

The present invention provides halophilic *Bacillus amyloliquefaciens* KMUS1 strain which is deposited as KCTC13635BP and produces thrombolytic enzyme nattokinase.

Preferably, the strain may be isolated from salted kimchi, but it is not limited thereto.

Preferably, the strain can be grown at a concentration of 0.5 to 10% NaCl and a temperature of 30 to 40° C., and more preferably, the strain can be optimally grown at a concentration of 5% NaCl and a temperature of 40° C., but it is not limited thereto.

Also, the present invention provides a method of producing thrombolytic enzyme nattokinase culturing the halophilic *Bacillus amyloliquefaciens* KMUS1 strain.

In addition, the present invention provides a food composition comprising a bacterial body, a culture obtained by culturing the halophilic *Bacillus amyloliquefaciens* KMUS1 strain, or an enzyme isolated and purified therefrom, as an active ingredient.

Preferably, the enzyme may be a thrombolytic enzyme nattokinase, but it is not limited thereto.

In the case of the food composition of the present invention, there is no particular limitation on the kind of the food. Examples of foods to which the active ingredient can be added include dairy products, meat, sausage, bread, chocolate, candy, snacks, confectionery, pizza, ramen, other noodles, gum, dairy products including ice cream, fermented products including kimchi and salted fish, various soups, beverages, teas, drinks, alcoholic beverages, vitamin complexes and the like.

In addition, the present invention provides a functional food composition comprising a bacterial body, a culture obtained by culturing the halophilic *Bacillus amyloliquefaciens* KMUS1 strain, or an enzyme isolated and purified therefrom, as an active ingredient.

In addition, the present invention provides a health functional food composition comprising a bacterial body, a culture obtained by culturing the halophilic *Bacillus amyloliquefaciens* KMUS1 strain, or an enzyme isolated and purified therefrom, as an active ingredient.

The health functional food composition of the present invention may be provided in the form of powder, granules, tablets, capsules, syrup, beverages or pills, and the health food composition is used with other foods or food additives in addition to the active ingredients of the present invention and it can be appropriately used depending on the method. The mixing amount of the active ingredient may be appropriately determined according to the purpose of use, for example, prevention, health or therapeutic treatment.

There are no specific restrictions on the types of health functional foods, examples of which include meat, sausage, bread, chocolate, candy, snacks, confectionery, pizza, ramen, other noodles, gum, dairy products including ice cream, various soups, beverages, tea, drinks, alcoholic beverages, vitamin complexes and the like.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

<Example 1> Identification of *Bacillus amyloliquefaciens* Strain

1. Isolation of Fermented Food Microorganisms

*Bacillus* was isolated from the purchased fermented food, salted kimchi. It was separated by pulverizing the fermented food, suspending 1 g of fermented food with physiological saline, and spreading 0.1 ml of the diluted suspension supernatant on a medium at salt concentration of 0.5%, 5%, 10% TSA (Tryptone 1.7%, Soytone 0.3%, Dextrose 0.25%, Sodium Chloride 0.5%, Dipotassium Phosphate 0.25%, Agar 1.5%) and incubating for 24 hours at 37° C. Among the cultured microorganisms, the bacteria with the best growth were selected in a 10% salt concentration medium.

2. Identification of Isolated Strains

DNA of the selected strain was extracted, 16s rRNA was amplified using 27F and 1492R primers, and the analyzed sequence information was identified using BLAST of NCBI (www.ncbi.nlm.nih.gov) to create the phylogenetic tree. As a result, the *Bacillus amyloliquefaciens* KMUS1 strain of the present invention could be identified (FIG. 1).

<Example 2> Comparison of Halophilicity with Other Strains

After incubating *Bacillus amyloliquefaciens* KMUS1 strain according to the present invention, the standard strain *Bacillus amyloliquefaciens* KCTC1660, and the standard strain *Bacillus subtilis* 168 (*B. subtilis* 168) strain in TSB medium to which 0.5%, 5%, 10%, 12%, 15% NaCl was added for 24 hours, absorbance was measured at 600 nm to measure the growth degree of each strain (FIG. 2). As can be seen in FIG. 2, it can be seen that the strain according to the present invention has a resistance to sodium chloride of 10% or more compared to the standard strains *Bacillus amyloliquefaciens* KCTC1660 and *Bacillus subtilis* 168.

<Example 3> Growth of *Bacillus amyloliquefaciens* KMUS1 According to Culture Temperature and Salt Concentration In order to establish the optimal culture conditions for the strain, culture was performed at various temperatures for 24 hours and 200 rpm. Temperature conditions were carried out at 30° C., 37° C., 40° C., the salt concentration was cultured at 0.5%, 5%. After incubation for 24 hours, the growth of the bacteria was measured at 600 nm.

FIG. 3A shows the growth of bacteria by temperature in a 0.5% sodium chloride medium and FIG. 3B shows the growth of bacteria by temperature in a 5% sodium chloride medium. The condition showing the maximum OD is 40° C. and 5% salt. From this, the strain exhibits optimal growth at 40° C. and 5% salt, and it can be said to be a halophilic bacteria as it shows optimal growth at a higher salt concentration than other strains.

<Example 4> Nattokinase Activity Produced by *Bacillus amyloliquefaciens* KMUS1

The isolated strain was inoculated into 50 ml of TSB medium, and the supernatant of the culture solution cultured at 37° C. for 24 hours was taken and centrifuged at 8,000 rpm for 20 minutes. For the nattokinase activity, enzyme activity was analyzed by measuring a low-molecular substance having a benzene ring produced by decomposition of fibrin at 275 nm.

*Bacillus amyloliquefaciens* KMUS1 strain of the present invention has a nattokinase enzyme activity of 24 FU/ml and a GGT enzyme activity of 0.67 U/ml. When compared with the standard strains *Bacillus amyloliquefaciens* KCTC 1660 strain and *Bacillus subtilis* 168 strain, it was found that the activity of nattokinase and GGT enzyme was excellent (Table 1).

TABLE 1

| Bacillus spp. | Nattokinase activity (FU/ml) | GGT activity (U/ml) |
|---|---|---|
| B. amyloliquefaciens KMUS1 | 24.0 | 0.67 |
| B. amyloliquefaciens KCTC$^T$ | 12.2 | 0.42 |
| B. subtilis 168$^T$ | 3.3 | 0.01 |

<Example 5> Comparison of Nattokinase Enzyme Activity According to Salt Concentration of Nattokinase Produced by *Bacillus amyloliquefaciens* KMUS1 Strain In order to establish the salt resistance of the nattokinase produced by the *Bacillus amyloliquefaciens* KMUS1 strain of the present invention, it was cultured at various salt concentrations (0.5%, 5%, 10%) for 24 hours and 200 rpm. After incubation, the supernatant was collected by centrifugation at 8,000 rpm for 20 minutes, and enzyme activity was measured.

FIG. 4 shows the activity of the nattokinase enzyme in various sodium chloride conditions, which compared with the standard strain *Bacillus amyloliquefaciens* KCTC 1660. The enzyme activity of nattokinase produced by the standard strain *Bacillus amyloliquefaciens* KCTC 1660 was maintained at 55% in 5% salt and at 3% in 10% salt, while the nattokinase enzyme activity *Bacillus amyloliquefaciens* KMUS1 strain of the present invention was maintained at 88% in 5% salt and 20% in 10% salt. From this, it can be said that the nattokinase of the KMUS1 strain is a halophilic enzyme.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of preparing a food product comprising a bacterial body, comprising:
   isolating *Bacillus* from a fermented food;
   spreading the isolated *Bacillus* on a medium having a NaCl concentration of 5%;
   incubating the medium at a temperature of 30 to 40° C.;
   selecting, from the incubated medium, a halophilic *Bacillus amyloliquefaciens* KMUS1 strain which is deposited as KCTC13635BP,
   wherein the selected KMUS1 strain exhibits optimal growth at the NaCl concentration of 5%; and
   adding the halophilic *Bacillus amyloliquefaciens* KMUS1 strain, as an active ingredient, into the food product selected from the group consisting of sausage, bread, chocolate, candy, snacks, confectionery, pizza, ramen, ice cream, alcoholic beverages, and vitamin complexes to prepare the food product comprising the bacterial body.

2. The method of claim 1, wherein a thrombolytic enzyme nattokinase is produced from the halophilic *Bacillus amyloliquefaciens* KMUS1 strain.

3. The method of claim 1, wherein the selected KMUS1 strain exhibits the optimal growth at the temperature of 40° C.

* * * * *